(12) United States Patent
Bang et al.

(10) Patent No.: US 12,692,222 B2
(45) Date of Patent: *Jul. 28, 2026

(54) METHOD OF FORMING A CHELATING COMPOSITION

(71) Applicant: NOURYON CHEMICALS INTERNATIONAL B.V., Amsterdam (NL)

(72) Inventors: Edwin Rudolf Antony Bang, Arnhem (NL); Martin Heus, Arnhem (NL); Tjerk Oedse Boonstra, Duiven (NL)

(73) Assignee: NOURYON CHEMICALS INTERNATIONAL B.V., Amsterdam (NL)

( * ) Notice: Subject to any disclaimer, the term of this patent is extended or adjusted under 35 U.S.C. 154(b) by 544 days.

This patent is subject to a terminal disclaimer.

(21) Appl. No.: 18/324,281

(22) Filed: May 26, 2023

(65) Prior Publication Data

US 2023/0382846 A1 Nov. 30, 2023

Related U.S. Application Data

(60) Provisional application No. 63/365,491, filed on May 30, 2022, provisional application No. 63/365,492, (Continued)

(51) Int. Cl.
*C07C 227/16* (2006.01)
*C07C 227/26* (2006.01)
(Continued)

(52) U.S. Cl.
CPC .......... *C07C 227/16* (2013.01); *C07C 227/26* (2013.01); *C07C 227/44* (2013.01); *C07C 229/24* (2013.01)

(58) Field of Classification Search
CPC ............................ C07C 227/16; C07C 227/26
See application file for complete search history.

(56) References Cited

U.S. PATENT DOCUMENTS 8,455,682 B2 6/2013 Oftring et al.
8,551,312 B2 10/2013 Heus et al.
(Continued)

FOREIGN PATENT DOCUMENTS

CN 101578258 B 1/2013
CN 109912440 A 6/2019
(Continued)

OTHER PUBLICATIONS

Othman Omro et al., Chelating agents usage in optimization of fracturing fluid rheology prepared from seawater, Polymers, vol. 13, No. 13, 2111, pp. 1-15—(Year: 2021).*
(Continued)

*Primary Examiner* — Yate' K Cutliff
(74) *Attorney, Agent, or Firm* — Ingrassia, Fisher & Lorenz, LLP

(57) ABSTRACT

A method includes combining monosodium glutamate and/or glutamic acid with formaldehyde to form a first combination; adding hydrogen cyanide to form a second combination comprising a monosodium salt of glutamic acid diacetonitrile, a cyclic GLMN, and a sodium salt of glutamic acid N-monoacetonitrile, maintaining a temperature of the second combination at less than about 16° C. and a pH of less than about 7; converting nitrile groups to carboxylate groups thereby forming a third combination comprising water and at least about 47 weight percent of the tetrasodium salt of GLDA, wherein a reaction yield is at least about 91%; providing a fourth combination comprising water and the
(Continued)

tetrasodium salt of GLDA and having a pH of less than about 7; and combining the third and fourth combinations to form the chelating composition.

6 Claims, 1 Drawing Sheet

Related U.S. Application Data filed on May 30, 2022, provisional application No. 63/365,493, filed on May 30, 2022.

(51) Int. Cl.
 *C07C 227/44* (2006.01)
 *C07C 229/24* (2006.01)

(56) References Cited

U.S. PATENT DOCUMENTS

| | | | | | |
|---|---|---|---|---|---|
| 2010/0126864 | A1* | 5/2010 | Heus | .................... | C07C 227/40 |
| | | | | | 204/522 |
| 2011/0257431 | A1* | 10/2011 | Baumann | .............. | C07C 229/16 |
| | | | | | 562/526 |
| 2015/0321995 | A1 | 11/2015 | Van Lare et al. | | |

FOREIGN PATENT DOCUMENTS

| | | | | | |
|---|---|---|---|---|---|
| EP | 1004571 | A1 | 5/2000 | | |
| JP | 10077253 | A | 3/1998 | | |
| JP | 2016522857 | A | 8/2016 | | |
| JP | 2017532421 | A | 11/2017 | | |
| JP | 2017535665 | A | 11/2017 | | |
| WO | WO-2009024518 | A1 * | 2/2009 | .............. | D21C 9/10 |
| WO | 2014191199 | A1 | 12/2014 | | |
| WO | 2016058872 | A1 | 4/2016 | | |
| WO | 2016083253 | A1 | 6/2016 | | |

OTHER PUBLICATIONS

Othman Amro et al: "Chelating Agents Usage in Optimization of Fracturing Fluid Rheology Prepared from Seawater", Polymers, vol. 13, No. 13, Jun. 27, 2021 (Jun. 27, 2021), p. 2111.

Anonymous: "Dissolvine", Nouryon—technical brochure, 2018, XP055935623, Retrieved from the Internet: URL:https://www.nouryon.com/globalassets/nouryon/1.-products/chelates/brochure-chelates-dissolvine-gl-global-en.pdf [retrieved on Jun. 27, 2022].

* cited by examiner

Linear Nitrile

Cyclic Nitrile

Formaline

HCN pH, T (MSG)

s-GLMN-Na e-GLMN-Na

NaOH

GLMA Cyclic By-Product

GLMA Linear By-Product

+ e-GLMA-Na$_2$ s-GLMA-Na$_3$

Formaline

HCN

NaOH

GLDN-Na

GLDA-Na$_4$

METHOD OF FORMING A CHELATING COMPOSITION

CROSS-REFERENCE TO RELATED APPLICATIONS

This application claims the benefit of U.S. Provisional Application No. 63/365,491, filed May 30, 2022, U.S. Provisional Application No. 63/365,492, filed May 30, 2022, and U.S. Provisional Application No. 63/365,493, filed May 30, 2022, each of which is hereby expressly incorporated herein in its entirety by reference.

TECHNICAL FIELD

The present disclosure generally relates to a method of forming a chelating composition comprising the tetrasodium salt of glutamic acid N,N-diacetic acid (GLDA). The chelating composition has a low viscosity while including a surprisingly high weight percent of the GLDA.

BACKGROUND

Several sodium salts of the chelating compound glutamic acid N,N-diacetic acid (GLDA) are known in the art. For instance, U.S. Pat. No. 8,455,682 describes the synthesis of GLDA tetrasodium salt using HCN and formaldehyde and glutamic acid or monosodium glutamate. The method makes use of ambient or elevated temperature (10-100° C.; especially 20-80° C.) and dosing times of 10 minutes to 10 hours but especially 30 minutes to 3 hrs. The process described is a two-step process in which first one equivalent formaldehyde is dosed to the pre-charged glutamate and in a 2nd step HCN and the other equivalent of formaldehyde are dosed.

Another HCN based GLDA process is described in WO 2009/024518, wherein examples result in mixed sodium/potassium salts of GLDA; GLDA-Na$_x$K$_y$ (x+y=4). In this reference, a two-step process at ambient or slightly elevated temperature is used. The first step describes the synthesis of a Schiff-base before applying a second dosing step in which remaining amounts of formaldehyde/HCN are added.

Typically, in the art, a yield on glutamate in GLDA-Na$_4$ processes using HCN/formaldehyde technology is from about 89 to about 94%. However, the art does not describe why the yield is limited. The only by-product which is typically described is NTA-Na$_3$ (nitrilotriacetic acid sodium salt) which is present at a level below about 0.1 wt % which does not explain why the yield based on glutamate/glutamic acid conversion is about 90%.

It is known in the art that handling GLDA tetrasodium salt solutions in high concentrations has some major drawbacks when used on a commercial scale. An important problem is the high viscosity of concentrated solutions of GLDA tetrasodium salt which makes such a solution difficult to handle. The high viscosity limits the practical concentration to maximum values of about 47 wt %. Today, at concentrations above about 55 to about 60 wt %, the GLDA tetrasodium salt tends to become a paste, making it necessary to heat containers before the product can be poured out. GLDA-Na$_4$ solutions do not typically crystallize when concentrated. It is simply the increasing viscosity that prevents use of higher concentrations.

Moreover, aqueous GLDA-Na$_4$ solutions tend to be corrosive to aluminum mainly due to a free caustic by-product in the GLDA solution. This therefore limits applications to corrosive-proof installations. These problems become particularly relevant when using GLDA-Na$_4$ solutions in large-scale productions having aluminum parts such as spray driers, especially when large containers of about 1,000 KG or more are used. Accordingly, there remains an opportunity for improvement.

BRIEF SUMMARY

This disclosure provides a method of forming a chelating composition, the method comprising the steps of: combining monosodium glutamate and/or glutamic acid (and/or glutamic acid and caustic) with formaldehyde to form a first combination; adding hydrogen cyanide to the first combination to form a second combination comprising a monosodium salt of glutamic acid diacetonitrile, a cyclic GLMN, and a sodium salt of glutamic acid N monoacetonitrile (and optionally and a sodium salt of glutamic acid N-monoacetonitrile), maintaining a temperature of the second combination at less than about 16° C. and a pH of less than about 7; converting nitrile groups of the monosodium salt of glutamic acid diacetonitrile to carboxylate groups thereby forming a third combination comprising water and at least about 47 weight percent of the tetrasodium salt of glutamic acid N,N-diacetic acid based on a total weight of the third combination as determined using an Fe-Total Sequestering Value, and wherein a reaction yield of MSG (or a mix of MSG and caustic or mix of glutamic acid and disodium salt of glutamic acid) after conversion into the nitrile groups of the monosodium salt of GLDN followed by saponification to form the tetrasodium salt of glutamic N,N-diacetic acid is at least about 91%; providing a fourth combination comprising water and the tetrasodium salt of glutamic acid N,N-diacetic acid and having a pH of less than about 7; and combining the third and fourth combinations to form the chelating composition having a pH of at least about 9 and a viscosity of less than about 1350 mPa·s measured at about 5° C., or less than about 350 mPa·s measured at about 20° C., each using a Brookfield DV II plus viscometer with spindle S18 and a temperature controlled bath and comprising at least about 45 weight percent of the tetrasodium salt of glutamic acid N,N-diacetic acid based on a total weight of the chelating composition as determined using an Fe-Total Sequestering Value. It is also contemplated that the skilled person may combine a low assay of the third combination with a high assay of acidified product or utilize 2 times an amount of a low assay and require more water evaporation.

This disclosure also provides a method of forming a chelating composition, the method comprising the steps of: combining monosodium glutamate and/or glutamic acid and about one equivalent of caustic (such as NaOH to lead to the in-situ formation of MSG) with formaldehyde to form a first combination; adding hydrogen cyanide to the first combination to form a second combination comprising a monosodium salt of glutamic acid diacetonitrile, a cyclic GLMN, and a sodium salt of glutamic acid N,-monoacetonitrile, maintaining a temperature of the second combination at less than about 16° C. and a pH of less than about 7; and converting nitrile groups of the monosodium salt of glutamic acid diacetonitrile to carboxylate groups thereby forming the chelating composition comprising water and at least about 47 weight percent of the tetrasodium salt of glutamic acid N,N-diacetic acid based on a total weight of the chelating composition as determined using an Fe-Total Sequestering Value, wherein the final chelating composition has a pH of greater than about 9 and a viscosity of less than about 1350 mPa·s measured at about 5° C. or less than 350 mPa·s measured at about 20° C. using a Brookfield DV II plus viscometer with spindle S18 and a temperature controlled bath, and wherein a reaction yield of MSG (or a mix of MSG and caustic or mix of glutamic acid and disodium salt of glutamic acid) after conversion into the nitrile groups of the monosodium salt of GLDN followed by saponification to form the tetrasodium salt of glutamic N,N-diacetic acid is at least about 91%.

In various embodiments, this disclosure increases sustainability and the ability to transport and package of aqueous chelant solutions using solutions that still allows handling at room temperature without being too viscous, as would be appreciated by one of skill in the art.

BRIEF DESCRIPTION OF THE DRAWINGS

The present disclosure will hereinafter be described in conjunction with the following FIGURE, wherein FIG. 1 is a synthetic scheme showing formation of the tetrasodium salt of glutamic acid N,N-diacetic acid and various by-products.

DETAILED DESCRIPTION

The following detailed description is merely exemplary in nature and is not intended to limit the current chelating composition and/or method of forming. Furthermore, there is no intention to be bound by any theory presented in the preceding background or the following detailed description.

Embodiments of the present disclosure are generally directed to chelating compositions and methods for forming the same. For the sake of brevity, conventional techniques related to chelating compositions may not be described in detail herein. Moreover, the various tasks and process steps described herein may be incorporated into a more comprehensive procedure or process having additional steps or functionality not described in detail herein. In particular, various steps in the manufacture of chelating compositions are well-known and so, in the interest of brevity, many conventional steps will only be mentioned briefly herein or will be omitted entirely without providing the well-known process details. In this disclosure, the terminology "about" can describe values ±0.1, 0.5, 1, 2, 3, 4, 5, 6, 7, 8, 9, or 10%, in various embodiments. Moreover, it is contemplated that, in various non-limiting embodiments, all values set forth herein may be alternatively described as approximate or "about." It is contemplated that all isomers and chiral options for each compound described herein are hereby expressly contemplated for use herein.

Moreover, it is contemplated that, in various non-limiting embodiments, it is to be appreciated that all numerical values as provided herein, save for the actual examples, are approximate values with endpoints or particular values intended to be read as "about" or "approximately" the value as recited.

Throughout this disclosure, the terminology percent "actives" is well recognized in the art and means the percent amount of active or actual compound or molecule present as compared to, for example, a total weight of a diluted solution of a solvent and such a compound. Some compounds, such as a solvent, are not described relative to a percent actives because it is well known to be approximately 100% actives. Any one or more of the values describe herein may be alternatively described as percent actives as would be understood by the skilled person.

In various embodiments, the terminology "free of" describes embodiments that include less than about 5, 4, 3, 2, 1, 0.5, or 0.1, weight percent (or weight percent actives) of the compound or element at issue using an appropriate weight basis as would be understood by one of skill in the art. In other embodiments, the terminology "free of" describes embodiments that have zero weight percent of the compound or element at issue.

The terminology "consists essentially of" may describe various non-limiting embodiments that are free of one or more optional compounds described herein and/or free of one or more polymers, surfactants, additives, solvents, etc.

It is to be understood that the subscripts of polymers are typically described as average values because the synthesis of polymers typically produces a distribution of various individual molecules.

The polymers and compositions disclosed herein may suitably comprise, consist of, or consist essentially of the components, elements, and process delineations described herein. The embodiments illustratively disclosed herein suitably may be practiced in the absence of any element which is not specifically disclosed herein.

In various embodiments, glutamic acid, monosodium glutamate and/or disodium glutamate or mixtures thereof can be starting materials for producing a GLDA sodium salt. It is known by the skilled person that, for example, glutamic acid also needs caustic to form a monosodium salt. For example, glutamic acid alone is typically not present because it cannot form a sodium salt. For example, glutamic acid alone is not used because it cannot form a nitrile sodium salt. However, a mixture of glutamic acid, MSG and disodium glutamic acid may be utilized. For example, a two-step reaction can be utilized wherein glutamate or glutamic acid are converted into GLDA. A first reaction may be the synthesis of a nitrile while a second reaction may be hydrolysis/saponification of a resulting nitrile.

In various embodiments, this disclosure provides a highly pure aqueous solution of a sodium salt of the chelating compound GLDA (glutamic acid N,N-diacetic acid) and a process for making such solution e.g. using a waste-free process without any required purification step.

In other embodiments, this disclosure provides an alternative for the aqueous solutions of the tetrasodium salt of commercially available GLDA that have an approximately equal viscosity to currently available commercial products but higher concentrations of GLDA than those same commercial products and having no or less corrosive properties. In other embodiments, the disclosure provides a product that can be handled in containers at ambient temperature wherein a solution has high purity and can be made using a waste free or waste-minimized process.

In still other embodiments, the disclosure provides aqueous solutions of sodium salts of GLDA of varying concentrations. In some embodiments, there is no need to use mixed sodium/potassium salts of GLDA which is a benefit as KOH is not as readily available and more expensive. Moreover, this can also reduce viscosity.

Typically, wherever pH is described herein, it is the pH of a 1 wt % actives solution.

Chelating Composition

In various embodiments, this disclosure provides a chelating composition having a pH of at least about 9 or 9.5 measured as an about 1 wt % solution. In various embodiments, the pH is from about 8 to about 14, about 8.5 to about 14, about 9 to about 14, about 9.5 to about 14, about 9.5 to about 12.5, about 9.5 to about 12, about 9.5 to about 11.5, about 9.5 to about 11, about 9.5 to about 10.5, about 9.5 to about 10, about 10 to about 12, about 10 to about 11.5, about 10 to about 11, about 11 to about 12, about 11 to about 11.5, or about 11.5 to about 12, measured as an about 1 wt % solution. Typically, pH is important because the skilled person appreciates that a pH value that is too high will be corrosive towards aluminum. Furthermore, a pH that is too high indicates the presence of free caustic or NaOH even in small concentrations (wt %) which will increase viscosity of the composition because its molecular weight is small relative to the large molecular weight of the tetrasodium salt of glutamic acid N,N-diacetic acid. In various non-limiting embodiments, all values and ranges of values, both whole and fractional, including and between the aforementioned values, are hereby expressly contemplated for use herein.

The chelating composition may be, include, consist essentially of, or consist of, water and a tetrasodium salt of glutamic acid N,N-diacetic acid (GLDA). In one embodiment, the terminology "consist essentially of" describes embodiments that are free of, or include less than 5, 4, 3, 2, 1, 0.5, or 0.1, weight percent based on a total weight of the composition, of one or more byproducts known to be produced when forming GLDA, such as those described below. In various non-limiting embodiments, all values and ranges of values, both whole and fractional, including and between the aforementioned values, are hereby expressly contemplated for use herein.

The synthesis of GLDA (and GLDN, which is a nitrile precursor of GLDA) is not 100% selective. The reaction of glutamic acid or monosodium glutamate or mixtures thereof with formaldehyde and cyanide results in a small amount of glycolate and formate formation but, as was recently discovered, also glutamic acid monoacetic acid and a byproduct called 1-pyrrolidineacetic acid, 2-carboxy-5-oxo sodium salt which can be described as GLMA cyclic. The GLMA cyclic does not sequester metal ions and contributes to viscosity, cost, yield loss and density. Another byproduct, GLMA linear, is a very weak chelating agent and also contributes to viscosity, density and yield loss. After identifying the by-products GLMA linear and GLMA cyclic, it became clear why historical reported yields on glutamate conversion to GLDA have been reported at a maximum of 94% (more commonly a 90% yield is reported). A high conversion of MSG or the conversion of a mixture of MGS-glutamic acid to GLDA is possible by utilizing additional HCN and formaldehyde. However, one possible consequence is that the NTA level may be too high (>0.1 wt %) due to formaldehyde and HCN in a saponification step reacting with $NH_3$ that is formed by the hydrolysis of the nitrile functionality. A challenge solved herein is to achieve a high conversion/high yield while keeping NTA at or below about 0.1 wt %

GLMA, which is glutamic acid mono acetic acid, is typically the main byproduct in the production of GLDA. Two GLMA isomers can be formed by saponification of corresponding nitrile precursors, which can be described as GLMN linear/open and GLMN cyclic. Structures of GLMN linear and GLMN cyclic are set forth in FIG. 1.

The synthesis of GLDN, as a nitrile precursor for GLDA, in high yield is a challenge. Since the nitrile mono-adduct GLMN can form a ring structure which will not open, the conditions during GLDN nitrile synthesis should be controlled such that GLMN concentration will be low and only present for a short time. Typically, the higher the GLMN linear concentration and the longer the residence time of reaction, the more cyclic GLMN will be formed. Temperature and pH are typically important as well. At higher temperatures, reactions occurs faster. This is not only true for the synthesis of GLDN but also for by-products such as cyclic GLMN. The most favorable reaction conditions are those that result in GLDN formation but limit cyclic GLMN formation, e.g. a low reaction temperature and a short residence time.

GLDA is unique among chelating agents because its nitrile precursor, used to synthesize high purity chelating agent, can form a ring structure. Such structures normally include or 6-atoms. When a mono-nitrile is formed, the hydrogen atom bonded to the nitrogen atom can still react with the carboxylic acid group while splitting off water resulting in the ring structure referred to as cyclic GLMN-Na. The structure of the mono-nitrile allows the formation of a ring structure which once formed will never become a GLDA sodium salt. A well-known product like MGDA, which is also a chelating agent, doesn't face this particular challenge because the mono-nitrile precursor of MGDA (methylglycine monoacetonitrile) is incapable of forming a ring structure.

In various embodiments, it was discovered that a low reaction temperature in the nitrile synthesis will reduce the formation of cyclic GLMN. A short residence time of GLMN linear is important too as it reduces the possibility of cyclic GLMN formation. One problem to overcome is the strong exothermic behavior of the nitrile synthesis. At the moment HCN is dosed, significant heat is generated thereby increasing the reaction temperature. Efficient cooling is required. The heat being developed depends on the amount of HCN. Slower dosing HCN helps to control the reaction temperature while cooling but it increases the residence time of high GLMN concentrations present during the GLDN synthesis. As a result, more cyclic GLMN is produced.

Referring back, in various embodiments, the chelating composition includes water present in an amount of from about 35 to about 50, about 35 to about 45, about 35 to about 40, about 40 to about 50, about 40 to about 45, about 41 to about 45, about 41 to about 44, about 41 to about 43, about 41 to about 42, or about 41, 42, 43, 44, or 45, weight percent when the GLDA is about 55 wt % concentrated having slightly more or less byproducts. As would be understood by those of skill in the art, the aforementioned values could change if the weight percent of the GLDA is changed. All of these possibilities are hereby expressly contemplated herein in various non-limiting embodiments. In other non-limiting embodiments, all values and ranges of values, both whole and fractional, including and between the aforementioned values, are hereby expressly contemplated for use herein.

The tetrasodium salt of the glutamic acid N,N-diacetic acid (GLDA) is present in an amount of at least about 45 weight percent based on a total weight of the chelating composition as determined using an Fe-Total Sequestering Value. In various embodiments, this weight percent is from about 45 to about 70, about 50 to about 70, about 55 to about 70, about 60 to about 65, about 50 to about 60, about 50 to about 65, about 50 to about 55, or about 55 to about 60, as determined using an Fe-Total Sequestering Value. In other embodiments, this weight percent is about 52 to about 60, about 53 to about 59, about 54 to about 58, about 55 to about 57, or about 55 to about 56, as determined using an Fe-Total Sequestering Value. In various non-limiting embodiments, all values and ranges of values, both whole and fractional, including and between the aforementioned values, are hereby expressly contemplated for use herein.

The method of determining weight percent based on the Fe-Total Sequestering Value is known in the art, e.g. as described by Dow Chemical relative to use of Versene™ chelating agents and as set forth in Appendix A.

Referring back, the chelating composition has a viscosity of less than about 1350 mPa·s measured at about 5° C. or less than about 350 mPa·s at about 20° C., each as measured using a Brookfield DV II plus viscometer with spindle S18 and a temperature controlled bath. In various embodiments, the viscosity is measured at a temperature of about 5° C. using a Brookfield DV II plus viscometer with spindle S18 and a temperature controlled bath. In such embodiments, the viscosity may be less than about 1350, 1300, 1250, 1200, 1150, 1100, 1050, 1000, mPa·s etc. In other embodiments, the viscosity is measured at a temperature of about 20° C. using a Brookfield DV II plus viscometer with spindle S18 and a temperature controlled bath. In such embodiments, the viscosity may be less than about 350, 300, 250, 200, 150, 100, mPa·s etc. In various non-limiting embodiments, all values and ranges of values, both whole and fractional, including and between the aforementioned values, are hereby expressly contemplated for use herein.

In other embodiments, the chelating composition can be described as non-corrosive as determined by United Nations Standard Recommendations on the transport of the dangerous goods, Manual of tests and criteria; ST/SG/AC.10/11/Rev 4. As is known in the art, this standard involves tested steel types of P3 (ISO 2604 (IV)-1975 or a comparable type, for aluminum 7075-T6 or AZSGU-T6 is required. Reliable measurement require a volume/surface area of >0.50 ml/mm$^2$. Materials used in this investigation are carbon steel SAE 1020 and aluminum 7075 T6. In various non-limiting embodiments, all values and ranges of values, both whole and fractional, including and between the aforementioned values, are hereby expressly contemplated for use herein.

In one embodiment, the viscosity is less than about 1200 mPa·s measured at about 5° C. using a Brookfield DV II plus viscometer with spindle S18 and a temperature controlled bath and the composition is classified as non-corrosive as determined by United Nations Standard Recommendations on the transport of the dangerous goods, Manual of tests and criteria; ST/SG/AC.10/11/Rev 4. In various non-limiting embodiments, all values and ranges of values, both whole and fractional, including and between the aforementioned values, are hereby expressly contemplated for use herein.

In other embodiments, the chelating composition has a density greater than about 1300, 1350, 1400, 1450, or even 1500, kg/m$^3$. In such embodiments, shipping volumes are highly attractive as shipping costs are reduced and CO$_2$ footprints are reduced. In various non-limiting embodiments, all values and ranges of values, both whole and fractional, including and between the aforementioned values, are hereby expressly contemplated for use herein.

In another embodiment, the pH of the chelating composition is from about 10 to about 10.5 measured as an about 1 wt % solution. In another embodiment, the pH of the chelating composition is from about 8 to about 10.5 measured as an about 1 wt % solution. In another embodiment, the pH of the chelating composition is from about 8.5 to about 10.5 measured as an about 1 wt % solution. In another embodiment, the pH of the chelating composition is from about 9 to about 10.5 measured as an about 1 wt % solution. In another embodiment, the pH of the chelating composition is from about 9.5 to about 10.5 measured as an about 1 wt % solution. In various non-limiting embodiments, all values and ranges of values, both whole and fractional, including and between the aforementioned values, are hereby expressly contemplated for use herein.

The aforementioned chelating composition can be formed by any method known in the art and is not limited. However, in one embodiment, the chelating composition is formed from combining: a first mixture comprising water and the tetrasodium salt of glutamic acid N,N-diacetic acid having a pH of greater than about 10; and a second mixture comprising water and the sodium salt of glutamic acid N,N-diacetic acid having a pH of less than about 7. In other embodiments, this pH can be less than about 8.5, 7, 7.5, 7, 6.5, 6, 5.5, or 5. As would be understood by the skilled person, weak ion exchange resins delivering a slightly higher pH solution can also be used too wherein using a less acidic product typically requires more volume/product to reduce the pH to target value and that typically changes the ratio non-acidified GLDA:acidified GLDA. In various non-limiting embodiments, all values and ranges of values, both whole and fractional, including and between the aforementioned values, are hereby expressly contemplated for use herein.

The first mixture may be, include, consist essentially of, or consist of, the water and the tetrasodium salt of glutamic acid N,N-diacetic acid. In various embodiments, the terminology "consist essentially of" describes embodiments that are free of, or include less than 5, 4, 3, 2, 1, or 0.1, weight percent based on a total weight of the composition, of one or more byproducts known to be produced when forming GLDA, such as those described herein. In various non-limiting embodiments, all values and ranges of values, both whole and fractional, including and between the aforementioned values, are hereby expressly contemplated for use herein.

In the first mixture, the amount of water is typically from about 0.1 to about 80, about 0.1 to about 75, about 0.1 to about 70, about 0.1 to about 65, about 0.1 to about 60, about 0.1 to about 55, about 0.1 to about 50, about 5 to about 45, about 10 to about 40, about 15 to about 35, about 20 to about 30, about 25 to about 30, about 0.1 to about 5, about 0.5 to about 5, or about 1, 2, 3, 4, or 5, weight percent based on a total weight percent of the first mixture. Also in the first mixture, the pH is typically greater than about 10.5, 11, 11.5, 12, etc. measured as an about 1 wt % solution. In various embodiments, this pH is from about 11 to about 12 measured as an about 1 wt % solution. The pH of the first mixture is typically important for the same reasons as described above. Moreover, in a formaldehyde/cyanide based manufacturing method involving saponification, this type of method in the last step delivers a GLDA solution having a small amount of free caustic. The excess caustic is needed to ensure all nitrile groups will be fully hydrolyzed. However, after hydrolysis, the free caustic should remain limited as otherwise neutralization by acidic GLDA will require more of the acidified GLDA product. Furthermore, a high free caustic level makes the GLDA solution more viscous. In various non-limiting embodiments, all values and ranges of values, both whole and fractional, including and between the aforementioned values, are hereby expressly contemplated for use herein.

Also in the first mixture, the amount of the tetrasodium salt of glutamic acid N,N-diacetic acid is typically from about 30 to about 60, about 35 to about 55, about 40 to about 50, or about 45 to about 50, weight percent based on a total weight percent of the first mixture. In various non-limiting embodiments, all values and ranges of values, both whole and fractional, including and between the aforementioned values, are hereby expressly contemplated for use herein.

The second mixture may be, include, consist essentially of, or consist of, the water and the sodium salt of glutamic acid N,N-diacetic acid. In various embodiments, the terminology "consist essentially of" describes embodiments that are free of, or include less than 5, 4, 3, 2, 1, 0.5 or 0.1, weight percent based on a total weight of the composition, of one or more byproducts known to be produced when forming GLDA, such as those described below. In various non-limiting embodiments, all values and ranges of values, both whole and fractional, including and between the aforementioned values, are hereby expressly contemplated for use herein.

In the second mixture, the amount of water is typically from about 35 to about 60, about 40 to about 55, or about 45 to about 50, weight percent based on a total weight percent of the second mixture. Also in the second mixture, the pH is typically less than about 7, 6.5, 6, 5.5, 5, 4.5, 4, 3.5, 3, etc. measured as an about 1 wt % solution In various embodiments, this pH is from about 3 to about 4, measured as an about 1 wt % solution. The pH of the second mixture is important as described above. Moreover, at too high of pH, the third mixture requires a high ratio of acidic GLDA to get pH ~9-10 which would require a larger volume of GLDA to be acidified In various non-limiting embodiments, all values and ranges of values, both whole and fractional, including and between the aforementioned values, are hereby expressly contemplated for use herein.

In various embodiments, the second mixture is acidified via ion exchange and/or bipolar membrane electrodialysis. This process may be or include any one or more steps described in at least U.S. Pat. No. 8,551,312B2 which is expressly incorporated herein in its entirety in various non-limiting embodiments.

Also in the second mixture, the amount of the sodium salt of glutamic acid N,N-diacetic acid (typically expressed as the tetrasodium salt or partially acidified GLDA sodium salt) is typically from about 15 to about 50, about 20 to about 35, or about 25 to about 30, weight percent based on a total weight of the chelating composition as determined using an Fe-Total Sequestering Value. In various non-limiting embodiments, all values and ranges of values, both whole and fractional, including and between the aforementioned values, are hereby expressly contemplated for use herein.

Method of Forming the Chelating Composition

In various embodiments, this disclosure describes the impact of two byproducts that have been identified on the viscosity and density profile of GLDA tetrasodium salt and the process to reduce the formation of these byproducts without introducing an extra purification step keeping the GLDA process waste free and as such meeting the sustainability targets of consumers. By-products present in solutions of chelating agents are often not capable of sequestering metal ions and even when capable they are less effective and disturb the performance of the main product. The presence of by-products is a good indication for the selectivity of a reaction. This means that the greater amount of by-products present correlated to a decreased yield of the final product, e.g. GLDA. For example, linear GLMA can sequester metals (such as Cu) but it does not sequester Fe such that linear GLMA does not impact/contribute to Fe-TSV measurements. Moreover, linear GLMA is a weaker chelating agent than GLDA.

A production process reducing the by-product level that results in higher purity GLDA would allow high concentrations of GLDA to be produced without viscosity or density becoming a barrier especially when free caustic is removed, e.g. by blending GLDA-Na$_4$ including free caustic with an acidified GLDA product in such a way that the free caustic concentration becomes zero or almost zero.

This disclosure provides a method of forming the chelating composition wherein the method includes the steps of: combining monosodium glutamate and/or glutamic acid and about one equivalent of caustic (such as NaOH to lead to the in-situ formation of MSG) with formaldehyde to form a first combination; adding hydrogen cyanide to the first combination to form a second combination comprising a monosodium salt of glutamic acid diacetonitrile, a cyclic GLMN, and a sodium salt of glutamic acid N,N'-monoacetonitrile; maintaining a temperature of the second combination at less than about 16° C. and a pH of less than about 7; converting nitrile groups of the monosodium salt of glutamic acid diacetonitrile to carboxylate groups thereby forming a third combination comprising water and at least about 47 weight percent of the tetrasodium salt of glutamic acid N,N-diacetic acid based on a total weight of the third combination as determined using an Fe-Total Sequestering Value, wherein the third combination has a pH of greater than about 10, and wherein a reaction yield of MSG (or a mix of MSG and caustic or mix of glutamic acid and disodium salt of glutamic acid) after conversion into the nitrile groups of the monosodium salt of GLDN followed by saponification to form the tetrasodium salt of glutamic N,N-diacetic acid is at least about 91%; providing a fourth combination comprising water and the tetrasodium salt of glutamic acid N,N-diacetic acid and having a pH of less than about 7; and combining the third and fourth combinations to form the chelating composition having a pH of at least about 8, 8.5, 9, or 9.5 and a viscosity of less than about 1350 mPa·s measured at about 5° C., or less than about 350 mPa·s measured at about 20° C., each using a Brookfield DV II plus viscometer with spindle S18 and a temperature controlled bath and comprising at least about 50 weight percent of the tetrasodium salt of glutamic acid N,N-diacetic acid based on a total weight of the chelating composition as determined using an Fe-Total Sequestering Value. In various non-limiting embodiments, all values and ranges of values, both whole and fractional, including and between the aforementioned values, are hereby expressly contemplated for use herein.

Referring to the step of combining monosodium glutamate and/or glutamic acid and about one equivalent of caustic (such as NaOH to lead to the in-situ formation of MSG) with formaldehyde to form a first combination, this step is not particularly limited in terms of order of addition, temperature, pressure, pH, time, etc. Typically, about 1 mole of monosodium glutamate and/or glutamic acid and about one equivalent of caustic (such as NaOH to lead to the in-situ formation of MSG) are combined with about 1.9 to about 2.2 moles of formaldehyde to form the first combination. A high excess of formaldehyde when combined with a high level of cyanide will result in a high level of the unwanted byproduct called NTA which is preferred to be less than about 0.1 wt percent in a final composition. When adding formaldehyde to the MSG the temperature typically should be below about 50, 45, 40, 35, 30, ° C. to minimize color formation. In various embodiments, a maximum temperature is about 30° C. In other embodiments, a temperature during the addition of formaldehyde is from about −10° C. to about 70° C., or any value or ranges of values therebetween. In various non-limiting embodiments, all values and ranges of values, both whole and fractional, including and between the aforementioned values, are hereby expressly contemplated for use herein.

Referring to the step of adding hydrogen cyanide to the first combination to form a second combination, again this step is not particularly limited in terms of order of addition, temperature, pressure, pH, time, etc. In various embodiments, the addition of HCN to the formaldehyde-MSG mixture should be completed at temperatures less than about 25, 20, 15, 10, or 5, ° C. Typically, about 1.9 to about 2.25 moles of hydrogen cyanide is added to the first combination to form the second combination. In various embodiments, when dosing the HCN the reaction temperature should less than about 25, 20, 15, 10, 5, 0, or −5, ° C. In various embodiments, the dosing speed of HCN should be maximized by applying cooling as a short dosing time gives a better quality product. In various non-limiting embodiments, the step of cooling is required. In various non-limiting embodiments, all values and ranges of values, both whole and fractional, including and between the aforementioned values, are hereby expressly contemplated for use herein.

The second combination may be, include, consist essentially of, or consist of, a monosodium salt of glutamic acid diacetonitrile, a cyclic GLMN (e.g. a cyclic GLMN sodium salt), and a sodium salt of glutamic acid N-monoacetonitrile. In various embodiments, the terminology "consist essentially of" describes that the second combination is free of, or includes less than 5, 4, 3, 2, 1, 0.5, or 0.1, weight percent of one or more reactants, impurities, or compounds that may or may not be those described above or herein, as would be understood by one of skill in the art. In various non-limiting embodiments, all values and ranges of values, both whole and fractional, including and between the aforementioned values, are hereby expressly contemplated for use herein.

In various embodiments, the monosodium salt of glutamic acid diacetonitrile is present in the second combination in an amount of at least about 30, 35, 40, 45, 50, 55, 60, 65, or weight percent based on a total weight of the second combination. In various non-limiting embodiments, all values and ranges of values, both whole and fractional, including and between the aforementioned values, are hereby expressly contemplated for use herein.

In various embodiments, the cyclic GLMN is present in the second combination in an amount of from about 0.1 to about 2.5, about 0.3 to about 0.1, or less than about 0.9, 0.8, 0.7, 0.5, 0.4, 0.3, 0.2, or 0.1, weight percent based on a total weight of the second combination. In various non-limiting embodiments, all values and ranges of values, both whole and fractional, including and between the aforementioned values, are hereby expressly contemplated for use herein.

In various embodiments, the sodium salt of glutamic acid N-monoacetonitrile is present in the second combination in an amount of from about 0.3 to about 1.5, about 0.3 to about 1, about 0.3 to about 0.5, or less than about 1.5, 1.25, 1, 0.75, 0.5, or 0.25, weight percent based on a total weight of the second combination. In various embodiments, a reaction temperature during HCN dosing is less than about 0° C., −5° C., or −7° C., such that a nitrile mixture gives a good quality GLDA after saponification. In various non-limiting embodiments, all values and ranges of values, both whole and fractional, including and between the aforementioned values, are hereby expressly contemplated for use herein.

Referring back to the step of maintaining a temperature of the second combination at less than about 16° C. and a pH of less than about 7, this step is also not particularly limited. For example, the temperature may be less than about 15, 10, 5, 0, or −5, ° C. and the pH may be less than about 6.5, 6, 5.5, 5, 4.5, 4, 3.5, 3, 2.5, 2, 1.5, 1, or 0.5. In other embodiments, this pH can be less than about 6.5, 6, 5.5, or 5. As is appreciated by the skilled person, the pH of the nitrile reaction has no connection to the pH of the GLDA as saponification takes place in a small excess of caustic. In various non-limiting embodiments, all values and ranges of values, both whole and fractional, including and between the aforementioned values, are hereby expressly contemplated for use herein.

Referring to the step of converting nitrile groups of the monosodium salt of glutamic acid diacetonitrile to carboxylate groups thereby forming a third combination, this step is also not particularly limited and may be defined as understood by one of skill in the art utilizing any appropriate reaction and/or mechanism.

The third combination may be, include, consist essentially of, or consist of water and at least about 47 weight percent of the tetrasodium salt of glutamic acid N,N-diacetic acid based on a total weight of the third combination as determined using an Fe-Total Sequestering Value. In various embodiments, the terminology "consist essentially of" describes that the third combination is free of, or includes less than 5, 4, 3, 2, 1, 0.5, or 0.1, weight percent of one or more reactants, impurities, or compounds that may or may not be those described above or herein, as would be understood by one of skill in the art. In various non-limiting embodiments, all values and ranges of values, both whole and fractional, including and between the aforementioned values, are hereby expressly contemplated for use herein.

In various embodiments, a mixture of the third and fourth combinations has a pH of greater than about 9, 9.5 or 10 and a viscosity of less than about 1350 mPa·s measured at about 5° C., or less than about 350 mPa·s measured at about 20° C., each using a Brookfield DV II plus viscometer with spindle S18 and a temperature controlled bath. In various embodiments, the pH is greater than about 10.5. Moreover, in other embodiments, the viscosity is less than about 1300, 1250, 1200, 1150, 1100, 1050, 1000, 950, 900, 850, 800, 750, etc. measured at about 5° C. using a Brookfield DV II plus viscometer with spindle S18 and a temperature controlled bath. In other embodiments, the viscosity is less than about 300, 250, 200, 150, 100, etc. measured at about 20° C. using a Brookfield DV II plus viscometer with spindle S18 and a temperature controlled bath. In various non-limiting embodiments, all values and ranges of values, both whole and fractional, including and between the aforementioned values, are hereby expressly contemplated for use herein.

In still other embodiments, a reaction yield of MSG (or a mix of MSG and caustic or mix of glutamic acid and disodium salt of glutamic acid) after conversion into the nitrile groups of the monosodium salt of GLDN followed by saponification to form the tetrasodium salt of glutamic N,N-diacetic acid is at least about 91, 92, 93, 94, 95, 96, 97, 98, or 99, %. To be clear, the yield of nitrile to GLDA (the saponification step) is ~100%. In various non-limiting embodiments, all values and ranges of values, both whole and fractional, including and between the aforementioned values, are hereby expressly contemplated for use herein.

Relative to the above, saponification can result in a product with these same properties. Saponification is required and is typically performed before combining the first and second mixtures. For example, a final solution may be or include a combination of GLDA having free caustic and acidified GLDA.

Referring back to the step of providing a fourth combination comprising water and the tetrasodium salt of glutamic acid N,N-diacetic acid and having a pH of less than about 7, again this step is not particularly limited and may be any known in the art. In other embodiments, this pH can be less than about 6.5, 6, 5.5, or 5. As would be understood by the skilled person, weak ion exchange resins delivering a slightly higher pH solution can also be used wherein using a less acidic product typically requires more volume/product to reduce the pH to a target value and that typically changes the ratio non-acidified GLDA:acidified GLDA. In various embodiments, the fourth combination may be, include, consist essentially of, or consist of, the water and the tetrasodium salt of glutamic acid N,N-diacetic acid. In various embodiments, the terminology "consist essentially of" describes that the fourth combination is free of, or includes less than 5, 4, 3, 2, 1, 0.5, or 0.1, weight percent of one or more reactants, impurities, or compounds that may or may not be those described above or herein, as would be understood by one of skill in the art. In various non-limiting embodiments, all values and ranges of values, both whole and fractional, including and between the aforementioned values, are hereby expressly contemplated for use herein. It is also contemplated that the skilled person can produce a GLDA high concentrate with low viscosity by using a high pH alkaline GLDA solution having free caustic and not combining it with an acidified GLDA solution but by treatment of the GLDA solution having free caustic directly using ion exchange or BPM technology.

In various embodiments, the tetrasodium salt of glutamic acid N,N-diacetic acid is present in the fourth combination in an amount of from about 30 to about 50, about 35 to about 45, or about 40 to about 45, weight percent based on a total weight of the fourth combination. In various non-limiting embodiments, all values and ranges of values, both whole and fractional, including and between the aforementioned values, are hereby expressly contemplated for use herein.

In various embodiments, the water is present in the fourth combination in an amount of from about 50 to about 70, about 55 to about 65, or about 60 to about 65, weight percent based on a total weight of the fourth combination. In various non-limiting embodiments, all values and ranges of values, both whole and fractional, including and between the afore-mentioned values, are hereby expressly contemplated for use herein.

Referring back, the method also includes the step of combining the third and fourth combinations to form the chelating composition having a pH of at least about 8, 8.5, 9, or 9.5 and a viscosity of less than about 1350 mPa·s measured at about 5° C., or less than about 350 mPa·s measured at about 20° C., each using a Brookfield DV II plus viscometer with spindle S18 and a temperature controlled bath and comprising at least about 50 weight percent of the tetrasodium salt of glutamic acid N,N-diacetic acid based on a total weight of the chelating composition as determined using an Fe-Total Sequestering Value. Each of the pH and viscosity values may be any as described herein. Similarly, the chelating composition may include at least about 50, 55, 65, 70, weight percent of the tetrasodium salt of glutamic acid N,N-diacetic acid based on a total weight of the chelating composition as determined using an Fe-Total Sequestering Value. In various non-limiting embodiments, all values and ranges of values, both whole and fractional, including and between the aforementioned values, are hereby expressly contemplated for use herein.

In one embodiment, the second combination comprises at least about 30, 35, 40, 45, or more weight percent of the monosodium salt of glutamic acid diacetonitrile based on a total weight of the second combination.

In another embodiment, the method further includes the step of evaporating water from the third combination such that the weight percent of the tetrasodium salt of glutamic acid N,N-diacetic acid in the chelating composition is at least about 47 weight percent based on a total weight of the chelating composition as determined using an Fe-Total Sequestering Value. In various embodiments, the chelating composition may include at least about 50, 55, 60, 65, or 70 weight percent of the tetrasodium salt of glutamic acid N,N-diacetic acid based on a total weight of the chelating composition as determined using an Fe-Total Sequestering Value. Water evaporation can also be done after combining the third and fourth combinations such that the final mixture has the desired concentration. In various non-limiting embodiments, all values and ranges of values, both whole and fractional, including and between the aforementioned values, are hereby expressly contemplated for use herein.

In another embodiment, the method further includes the step of maintaining the temperature of the first combination at less than about 25, 20, 15, or 10, ° C. In various embodiments, this temperature is less than about 11, 10, 9, 8, 7, 6, 5, 4, 3, 2, or 1, ° C. In still other embodiments, the temperature is about −15, −10, −5, or 0, ° C. In various non-limiting embodiments, all values and ranges of values, both whole and fractional, including and between the afore-mentioned values, are hereby expressly contemplated for use herein.

In another embodiment, a temperature of the second combination is maintained at less than about 20, 15, or 10° C. and the hydrogen cyanide is added to the first combination for a total time of about 15 to about 120 minutes. In various embodiments, this temperature is less than about 10, 9, 8, 7, 6, 5, 4, 3, 2, or 1, ° C. In other embodiments, this time is from about 20 to about 115, about 25 to about 110, about 30 to about 105, about 35 to about 100, about 40 to about 95, about 45 to about 90, about 50 to about 85, about 55 to about 80, about 60 to about 75, or about 65 to about 70, minutes. In various non-limiting embodiments, all values and ranges of values, both whole and fractional, including and between the aforementioned values, are hereby expressly contemplated for use herein.

In another embodiment, the third combination optionally further comprises sodium hydroxide and/or a nitrilotriacetic acid sodium salt (typically formed as an unwanted byproduct and not added), has a pH of at least about 11, and comprises less than about 0.5 weight percent of the cyclic GLMA; less than about 0.5 weight percent of the sodium salt of glutamic acid N,N'-monoacetonitrile; less than about 0.75 weight percent of the sodium hydroxide based on a total weight of the third combination; and less than about 0.1 weight percent of the nitrilotriacetic acid sodium salt based on a total weight of the third combination. Typically, free sodium hydroxide is present because a molar excess of sodium hydroxide is typically needed when saponifying the nitrile. In later steps, sodium hydroxide can be removed by combining with an acidified GLDA solution or can be acidified by any other method known in the art. In various non-limiting embodiments, all values and ranges of values, both whole and fractional, including and between the afore-mentioned values, are hereby expressly contemplated for use herein.

In another embodiment, the chelating composition optionally further comprises sodium hydroxide and/or a nitrilotriacetic acid sodium salt, has a pH of at least about 10, and includes less than about 0.75 weight percent of the cyclic GLMA based on a total weight of the chelating composition; less than about 0.5 weight percent of the sodium salt of glutamic acid N,N'-monoacetic acid based on a total weight of the chelating composition; less than about 0.5 weight percent of the sodium hydroxide based on a total weight of the chelating composition; and less than about 0.1 weight percent of the nitrilotriacetic acid sodium salt based on a total weight of the chelating composition. In various non-limiting embodiments, all values and ranges of values, both whole and fractional, including and between the aforementioned values, are hereby expressly contemplated for use herein.

In another embodiment, the third combination comprises sodium hydroxide and the method further comprises the step of acidifying the third combination via ion exchange and/or bipolar membrane electrodialysis to reduce a residual amount of the sodium hydroxide in the third combination. This may be completed using any method known in the art or described herein.

In another embodiment, the pH of the chelating composition is from about 10 to about 11 and the chelating composition comprises less than about 0.1 weight percent of NaOH based on a total weight of the chelating composition. In various non-limiting embodiments, all values and ranges of values, both whole and fractional, including and between the aforementioned values, are hereby expressly contemplated for use herein.

In another embodiment, the tetrasodium salt of glutamic acid N,N-diacetic acid present in the third combination in an amount of from about 47 to about 60 (e.g. about 54, 55, 56, 57, 58, 59, or 60) weight percent based on a total weight of the third combination as determined using an Fe-Total Sequestering Value. In various non-limiting embodiments, all values and ranges of values, both whole and fractional, including and between the aforementioned values, are hereby expressly contemplated for use herein.

In another embodiment, the tetrasodium salt of glutamic acid N,N-diacetic acid is present in the chelating composition in an amount of from about 47 to about 60 (e.g. about 47, 48, 49, 50, 51, 52, 53, 54, 55, 56, 57, 58, 59, or 60) weight percent based on a total weight of the chelating composition as determined using an Fe-Total Sequestering Value. In various non-limiting embodiments, all values and ranges of values, both whole and fractional, including and between the aforementioned values, are hereby expressly contemplated for use herein.

In another embodiment, the composition is non-corrosive as determined by United Nations Standard Recommendations on the transport of the dangerous goods, Manual of tests and criteria; ST/SG/AC.10/11/Rev 4.

In another embodiment, the reaction yield of the nitrile groups of the monosodium salt of glutamic acid diacetonitrile to form the tetrasodium salt of glutamic acid N,N-diacetic acid is at least about 95, 96, 97, 98, or 99, wt %. In various non-limiting embodiments, all values and ranges of values, both whole and fractional, including and between the aforementioned values, are hereby expressly contemplated for use herein.

In another embodiment, the reaction yield of the nitrile groups of the monosodium salt of glutamic acid diacetonitrile to form the tetrasodium salt of glutamic acid N,N-diacetic acid is at least about 95, 96, 97, 98, or 99%, and the chelating composition has a higher sequestration value as determined by Fe-total sequestering value (Fe-TSV) than a comparative chelating composition that includes greater than about 0.75 weight percent of the cyclic GLMN based on a total weight of the chelating composition as determined using an Fe-Total Sequestering Value and/or greater than about 0.75 weight percent of the sodium salt of glutamic acid N,N'-monoacetic acid. In various non-limiting embodiments, all values and ranges of values, both whole and fractional, including and between the aforementioned values, are hereby expressly contemplated for use herein.

In various embodiments, utilizing a heatsink before dosing HCN can be beneficial. However, use of an over diluted system is not efficient in the saponification process. Cooling a glutamate/glutamic acid solution or slurry and/or mixture of glutamate-formaldehyde solution before dosing HCN can be used to control reaction temperature. For example, one can simply start at a low temperature. A more efficient approach can include cooling of a glutamate/formaldehyde solution when all formaldehyde (which is 37% or 44 or 50 wt %) needed to synthesize GLDA has already been dosed. In one embodiment, warm formaldehyde (>25° C.) is cooled before HCN dosing starts and a larger reaction volume is cooled to a temperature below about 20° C., typically below about 10° C., and most typically to about 5, 0, −5, or −10, ° C., before any HCN addition will take place. Typically, an MSG-formaldehyde solution is cooled before dosing HCN because the MSG-formaldehyde solution gets warm because formaldehyde storage temperature depends on the concentration of formaldehyde. In various non-limiting embodiments, all values and ranges of values, both whole and fractional, including and between the aforementioned values, are hereby expressly contemplated for use herein.

In various embodiments, to this cold glutamate/formaldehyde solution or slurry (e.g. at a temperature 5-8° C.) cold HCN is dosed at the highest speed possible such that the reaction mixture will stay below about 15° C., preferably below about 10° C. or even about 5-8, or about 0, −5, or −10, ° C. An efficient cooling system is essential to control temperature because the reaction in which a nitrile is formed is highly exothermic. When all HCN is dosed, the reaction mixture is allowed to increase to a maximum of about 30, 35, or 40, ° C. depending on time as conversion of last traces of raw material tends to depend on a combination of time and temperature. In various non-limiting embodiments, all values and ranges of values, both whole and fractional, including and between the aforementioned values, are hereby expressly contemplated for use herein.

Additional Method of Forming the Chelating Composition

This disclosure also provides an additional method of forming the chelating composition, wherein the method includes the step of combining monosodium glutamate and/or glutamic acid and about one equivalent of caustic (such as NaOH to lead to the in-situ formation of MSG) with formaldehyde to form a first combination, adding hydrogen cyanide to the first combination to form a second combination comprising a monosodium salt of glutamic acid diacetonitrile, a cyclic GLMN, and a sodium salt of glutamic acid N-monoacetonitrile, maintaining a temperature of the second combination at less than about 16° C. and a pH of less than about 7; and converting nitrile groups of the monosodium salt of glutamic acid diacetonitrile to carboxylate groups thereby forming the chelating composition comprising water and at least about 47 weight percent of the tetrasodium salt of glutamic acid N,N-diacetic acid based on a total weight of the chelating composition as determined using an Fe-Total Sequestering Value, wherein the chelating composition has a pH of greater than about 10.5, and wherein a reaction yield of MSG (or a mix of MSG and caustic or mix of glutamic acid and disodium salt of glutamic acid) after conversion into the nitrile groups of the monosodium salt of GLDN followed by saponification to form the tetrasodium salt of glutamic N,N-diacetic acid is at least about 91%. Any one or more of the aforementioned steps, compounds, mixtures, conditions, etc. may be alternatively as described above. In various non-limiting embodiments, all values and ranges of values, both whole and fractional, including and between the aforementioned values, are hereby expressly contemplated for use herein.

In one embodiment, the second combination comprises from about 37 to about 50 weight percent of the monosodium salt of glutamic acid diacetonitrile based on a total weight of the second combination and depending on the concentration of MSG (and formaldehyde as HCN is 100% pure), as understood by the skilled person. In various non-limiting embodiments, all values and ranges of values, both whole and fractional, including and between the aforementioned values, are hereby expressly contemplated for use herein.

In another embodiment, the method further includes the step of evaporating water from the chelating composition such that the weight percent of the tetrasodium salt of glutamic acid N,N-diacetic acid in the chelating composition is at least about 47 weight percent based on a total weight of the chelating composition as determined using an Fe-Total Sequestering Value.

In another embodiment, the tetrasodium salt of glutamic acid N,N-diacetic acid is present in the chelating composition in an amount of from about 47 to about 60 weight percent based on a total weight of the chelating composition as determined using an Fe-Total Sequestering Value. In various non-limiting embodiments, all values and ranges of values, both whole and fractional, including and between the aforementioned values, are hereby expressly contemplated for use herein.

In another embodiment, the method further includes the step of maintaining the temperature of the first combination at less than about 25, 20, 16, 15, 14, 13, 12, 11, 10, 9, 8, 7, 6, 5, 4, 3, 2, or 1, ° C. In various non-limiting embodiments, all values and ranges of values, both whole and fractional, including and between the aforementioned values, are hereby expressly contemplated for use herein.

In another embodiment, a temperature of the second combination is maintained at less than about 10° C. and wherein the hydrogen cyanide is added to the first combination for a total time of about 15 to about 120 minutes. In various non-limiting embodiments, all values and ranges of values, both whole and fractional, including and between the aforementioned values, are hereby expressly contemplated for use herein.

In another embodiment, the chelating composition optionally further comprises sodium hydroxide and/or a nitrilotriacetic acid sodium salt, has a pH of at least about 11, and includes less than about 1 weight percent of the cyclic GLMA based on a total weight of the chelating composition; less than about 1 weight percent of the sodium salt of glutamic acid N,N'-monoacetic acid; less than about 1 or 0.75 weight percent of the sodium hydroxide; and less than about 0.1 weight percent of the nitrilotriacetic acid sodium salt based on a total weight of the chelating composition. In various non-limiting embodiments, all values and ranges of values, both whole and fractional, including and between the aforementioned values, are hereby expressly contemplated for use herein.

In another embodiment, the viscosity is less than about 1200 mPa·s at about 5° C. and the composition is classified as non-corrosive as determined by United Nations Standard Recommendations on the transport of the dangerous goods, Manual of tests and criteria; ST/SG/AC 0.10/11/Rev 4.

In another embodiment, the chelating composition comprises sodium hydroxide and the method further comprises the step of acidifying the chelating composition via ion exchange and/or bipolar membrane electrodialysis to reduce a residual amount of the sodium hydroxide in the chelating composition.

In another embodiment, the pH of the chelating composition is from about 9, 9.5, or to about 11, as a 1% solution, and the chelating composition comprises less than about 0.1 weight percent of NaOH based on a total weight of the chelating composition. In various non-limiting embodiments, all values and ranges of values, both whole and fractional, including and between the aforementioned values, are hereby expressly contemplated for use herein.

In another embodiment, the composition is non-corrosive as determined by United Nations Standard Recommendations on the transport of the dangerous goods, Manual of tests and criteria; ST/SG/AC.10/11/Rev 4.

In another embodiment, the reaction yield of the nitrile groups of the monosodium salt of glutamic acid diacetonitrile to form the tetrasodium salt of glutamic acid N,N-diacetic acid is at least about 90 or 95%.

In another embodiment, the reaction yield of the nitrile groups of the monosodium salt of glutamic acid diacetonitrile based on MSG and followed by saponification is at least about 95%, and the chelating composition has a higher sequestration value as determined by Fe-total sequestering value (Fe-TSV) than a comparative chelating composition that includes greater than about 1 weight percent of the cyclic GLMN based on a total weight of the chelating composition as determined using an Fe-Total Sequestering Value and/or greater than about 1 weight percent of the sodium salt of glutamic acid N,N'-monoacetonitrile based on a total weight of the chelating composition as determined using an Fe-Total Sequestering Value. Alternatively, in another embodiment, the chelating composition has a lower viscosity than an GLDA solution that has the same TSV and more MGMA.

Additional Embodiments

This disclosure provides a method of forming a chelating composition, the method comprising the steps of: combining monosodium glutamate and/or glutamic acid (and/or glutamic acid and caustic) with 2 equivalents of formaldehyde to form a first combination; adding about 2 equivalents of hydrogen cyanide to the first combination to form a second combination comprising a monosodium salt of glutamic acid diacetonitrile, a cyclic GLMN, and a sodium salt of glutamic acid N-monoacetonitrile (and optionally and a sodium salt of glutamic acid N-monoacetonitrile), maintaining a temperature of the second combination at less than about 16° C. and a pH of less than about 7; converting nitrile groups of the monosodium salt of glutamic acid diacetonitrile to carboxylate groups thereby forming a third combination comprising water and at least about 47 weight percent of the tetrasodium salt of glutamic acid N,N-diacetic acid based on a total weight of the third combination as determined using an Fe-Total Sequestering Value, and wherein a reaction yield of MSG (or a mix of MSG and caustic or mix of glutamic acid and disodium salt of glutamic acid) after conversion into the nitrile groups of the monosodium salt of GLDN followed by saponification to form the tetrasodium salt of glutamic N,N-diacetic acid is at least about 91%; providing a fourth combination comprising water and the tetrasodium salt of glutamic acid N,N-diacetic acid and having a pH of less than about 7; and combining the third and fourth combinations to form the chelating composition having a pH of at least about 9 and a viscosity of less than about 1350 mPa·s measured at about 5° C., or less than about 350 mPa·s measured at about 20° C., each using a Brookfield DV II plus viscometer with spindle S18 and a temperature controlled bath and comprising at least about 50 weight percent of the tetrasodium salt of glutamic acid N,N-diacetic acid based on a total weight of the chelating composition as determined using an Fe-Total Sequestering Value. It is also contemplated that the skilled person may combine a low assay of the third combination with a high assay of acidified product or utilize 2 times an amount of a low assay and require more water evaporation.

In other embodiments, other dosing profiles of HCN/ formaldehyde are also possible, see for example U.S. Pat. No. 8,455,682, which is expressly incorporated herein by references in its entirety in various non-limiting embodiments. In one or more non-limiting embodiments, a low temperature in a nitrile reaction mix and a short residence time of the mononitrile are important aspects.

Examples

Synthesis of GLMA cyclic (1-pyrrolidineacetic acid, 2-carboxy-5-oxo sodium salt)

The synthesis of 1-pyrrolidineacetic acid, 2-carboxy-5-oxo sodium salt, referred to as GLMA cyclic, is given below.

Into a 250 ml three necked round bottom flask equipped with a strong stirring bar, reflux condenser and nitrogen inlet capillary successively 29.72 g (200 mmoles) of L-glutamic acid and 16.24 g (400 mmol) of caustic microprills were charged. Under cooling using a water bath 60 ml of distilled water were added. All solids rapidly dissolved under strong evolution of heat. Thus an aqueous solution of disodium-L-glutamate was manufactured. After the reaction mixture cooled to ambient temperature 19.70 g (202 mmoles) of an aqueous glyconitrile solution (58.5 wt-%) have been added. A delayed weak evolution of heat was noticeable (about 25° C.).

After stirring for an hour (completing GLMN formation) another 8.24 g (203 mmoles) of caustic microprills were added portionwise under cooling. A moderate evolution of reaction heat and a change of color to a slightly yellowish tone was noticed. Stirring at room temperature was continued for one hour. Then the reaction mixture was heated to about 100° C. for 3 hours under nitrogen stripping (supporting the evolution of ammonia from nitrile hydrolysis). After cooling a slightly yellow aqueous solution of trisodium L-GLMA (pH 11.5) was obtained which apparently showed almost no more ammonia odor.

Under cooling with a water bath 60.43 g (605 mmol) of concentrated hydrochloric acid were added swiftly. After the addition was complete this mixture is refluxed for 4 hours. After cooling this mixture was poured over a glass filter (por. 1) into a 500 ml pear shaped round bottom flask. The mixture was evaporated to dryness using a rotavap. The residing hard mass was stirred with 100 ml of dry acetone. The inherent sodium chloride begins to coagulate and slowly began to crystallize. The salt (35.75 g, theory: 35.24 g) was removed using a glass frit (por. 3) and washed with acetone. The acetone phases were evaporated to dryness using a rotavap. Thus an extremely sticky yellowish oil (41.92 g) of c-GLMA-H$_2$ was obtained.

This residue was dissolved in 50 ml of water and 16.24 (400 mmol) of NaOH microprills, dissolved in 50 ml water, were added. After filtration into a 500 ml pear shaped flask this solution again was evaporated to dryness using a rotavap. The residue was extracted with 100 ml of absolute Ethanol. The solids were filtered off using a glass frit (por. 1) and washed once with ml of absolute ethanol and vacuum dried at 40° C. overnight. In this way 45.59 g of a colorless solid powder were obtained. Analysis by proton NMR and KarlFisher gave the following result: 84.6 wt % cyclic GLMA-Na$_2$, 3.5 wt % water; balance: small amounts of various by-products.

The product was tested on its sequestering capabilities by titration using Fe ions and Ca ions. These analytical procedures are known as Fe-total sequestering value (Fe-TSV) and Calcium chelating value (CaCV). The GLMA cyclic does not have any sequestering value and does not add anything to the assay of a GLDA in terms of sequestering capacity. At best, this compound can be considered as inert by-product.

Synthesis of GLMA linear

The synthesis of glutamic acid N,N-monoacetic acid sodium salt (linear GLMA) is given below.

Into a 250 ml three necked round bottom flask equipped with a strong stirring bar, reflux condenser and nitrogen inlet capillary successively 14.86 g (100 mmoles) of L-glutamic acid and 8.12 g (200 mmol) of caustic microprills were charged. Under cooling using a water bath 30 ml of distilled water were added. All solids rapidly dissolved under strong evolution of heat. Thus an aqueous solution of disodium-L-glutamate was manufactured. After the reaction mixture cooled to ambient temperature 9.75 g (100 mmoles) of an aqueous glyconitrile solution (58.5 wt-%) have been added. A delayed weak evolution of heat was noticeable (about 25° C.).

After stirring for an hour (completing GLMN formation) another 4.06 g (100 mmoles) of caustic microprills were added portionwise under cooling. A moderate evolution of reaction heat and a change of color to a slightly yellowish tone was noticed. Stirring at room temperature was continued for one hour. Then the reaction mixture was heated to about 100° C. for 3 hours under nitrogen stripping (supporting the evolution of ammonia from nitrile hydrolysis). After cooling a slightly yellow aqueous solution of trisodium L-GLMA (pH≈11.5) was obtained which apparently showed almost no more ammonia odor.

This mixture was poured over a glass filter (por. 1) into a 500 ml pear shaped round bottom flask and evaporated to dryness using a rotavap. The residing hard mass was stirred with 100 ml of absolute ethanol in order to remove most of the inherent water. After drying the residue was further extracted with 100 ml of methanol at 40° C. and filtered warm in order to remove traces of glutamate. After drying 29.47 g (theory: 27.24 g) of a colorless solid material were obtained.

Analysis by proton NMR and Karl Fisher gave the following result: 81.94 wt % open/linear GLMA-Na$_3$, 0.2 wt % GLDA-Na$_4$, 12 wt % water (Karl Fisher), and balance: small amounts of various byproducts.

It is expected that this by-product, based on structure, would have some sequestering power. The structure fragment responsible for sequestration are the two carboxylic acid groups attached to the nitrogen: —NH(CH2-COONa)$_2$. A strong chelation would require 3 carboxylic acid groups e.g. NTA-Na$_3$, nitrilotriacetic acid sodium salt [N—(CH2-COONa)$_3$]—a well-known chelating agent. Molecules with 2 carboxylic acids will contribute to sequestering power/ capacity but in a less efficient way e.g. sequestration of Cu ions is possible but not Fe3+ For that reason it is preferred to have low level of GLMA linear in the GLDA solution.

It is shown that GLMA linear has some sequestering power but it is less efficient compared to GLDA itself. Also this byproduct adds to viscosity/density and should be reduced as much as possible.

Synthesis of GLDA-Na$_4$ (55 wt %)

A 1 liter glass reactor vessel was loaded with 278 gram of MSG.H$_2$O (1.49 moles). The MSG was mixed with 220 grams water resulting in a 50.5 wt % MSG slurry. Two equivalents formaldehyde, 208.9 grams of 44.6% formaldehyde (3.11 moles) were dosed in 5 minutes. Subsequently the mixture was allowed to cool down to approximately 6° C. Then 2 equivalents of HCN, i.e. 82.5 gram (3.05 moles) were dosed in 45 minutes. The reaction temperature was kept at maximum 8° C.

When dosing of all formaldehyde and cyanide is completed, the glutamate is converted into the monosodium salt of glutamic acid diacetonitrile (referred to as GLDN) and small amounts of GLMN linear and GLMN cyclic. After HCN dosing, the mixture is stored for at least 30 minutes at ambient temperature to improve yield/conversion into GLDN.

The GLDN is dosed in a subsequent step reactor to pre-charged caustic/water at 96° C. and the nitrile groups are converted into carboxylate. When the GLDN dosing is completed the temperature of reaction mixture is increased to boiling temperature. During this reaction $NH_3$ is released. The hydrolysis or saponification at boiling temperature continues until ammonia release stops.

The GLDA sodium salt solution is concentrated until the desired concentration of 55 wt % is reached based on Fe-total sequestering value by evaporation of water. When needed, the color of the GLDA solution can be reduced by applying techniques such as using an active carbon column or bleaching with air/ozone/hydrogen peroxide. Analysis of the GLDA solution using proton NMR revealed the presence of 0.45 wt % GLMA linear and 0.37% GLMA cyclic. The free caustic concentration was 0.5 wt % and NTA <0.1 wt %. The pH=11.3 as a 1% solution. The GLDA yield on glutamate is 96.5% based on Fe-TSV. The density of the 55 wt % solution is 1435 kg at 20° C.

Acidification using ion exchange or bipolar membrane electrodialysis can eliminate the residual amount of free caustic. Free caustic needed in the saponification step is known to contribute to viscosity. When available, the skilled person can also add acidified GLDA. The effect of free caustic removal on the viscosity is visible by comparing viscosity profile/curve with and without free caustic, see below

Comparative Example

A $Na_4$-GLDA solution having a concentration of 55.0 wt % of $Na_3$-HEDTA expressed as a Fe-TSV value (Iron Total Sequestering Value) was made by dosing 1 equivalent formaldehyde to pre-charged sodium glutamate at a temperature of less than about 25° C. When dosing was complete the first equivalent of HCN was added in 45 minutes keeping the reaction mixture at a temperature of less than about 30° C.

In the next step, a second equivalent of formaldehyde and 2 equivalent of HCN are dosed simultaneously keeping the reaction temperature at a maximum of about 30° C. When all HCN and formaldehyde is completed, the mixture is stirred for another 30 minutes at about 25 to about 30° C.

The GLDN solution is dosed in a subsequent step reactor to pre-charged caustic/water at 96 C and the nitrile groups are converted into carboxylate. When the GLDN dosing is completed the temperature of reaction mixture is increased to boiling temperature. When the GLDN dosing is completed the temperature of reaction mixture is increased to boiling temperature. During this reaction NH3 is released. The hydrolysis or saponification at boiling temperature continues until ammonia release stops.

The GLDA sodium salt solution is concentrated until the desired concentration being 55 wt % based on Fe-total sequestering value by evaporation of water. Analysis using proton NMR revealed the presence of 1.8 wt % GLMA linear and 2.9 wt % GLMA cyclic. The free caustic concentration was 0.7 wt % and NTA <0.1 wt %. The pH=11.3. The GLDA yield on glutamate based on Fe-TSV is 89%. It is contemplated that the viscosity will drop when removing the free caustic by addition of acidified GLDA in such a way that the free caustic level becomes zero.

While at least one exemplary embodiment was presented in the foregoing detailed description, it should be appreciated that a vast number of variations exist. It should also be appreciated that the exemplary embodiment or exemplary embodiments are only examples, and are not intended to limit the scope, applicability, or configuration in any way. Rather, the foregoing detailed description will provide those skilled in the art with a convenient road map for implementing an exemplary embodiment. It being understood that various changes may be made in the function and arrangement of elements described in an exemplary embodiment without departing from the scope as set forth in the appended claims.

What is claimed is:

1. A method of forming a chelating composition, said method comprising the steps of:

combining monosodium glutamate and/or glutamic acid with formaldehyde to form a first combination;

adding hydrogen cyanide to the first combination to form a second combination comprising a monosodium salt of glutamic acid diacetonitrile, a cyclic GLMN, and a sodium salt of glutamic acid N,N'-monoacetonitrile, maintaining a temperature of the second combination at less than about 16° C. and a pH of less than about 7; and converting nitrile groups of the monosodium salt of glutamic acid diacetonitrile to carboxylate groups thereby forming the chelating composition comprising water and at least about 47 weight percent of the tetrasodium salt of glutamic acid N,N-diacetic acid based on a total weight of the chelating composition as determined using an Fe-Total Sequestering Value, wherein the chelating composition has a pH of greater than about 9 and a viscosity of less than about 1350 mPa·s measured at about 5° C. or less than 350 mPa·s measured at about 20° C. using a Brookfield DV II plus viscometer with spindle S18 and a temperature controlled bath, and wherein a reaction yield of MSG after conversion into the nitrile groups of the monosodium salt of GLDN followed by saponification to form the tetrasodium salt of glutamic N,N-diacetic acid is at least about 91%.

2. The method of claim 1 further comprising the step of evaporating water from the chelating composition such that the weight percent of the tetrasodium salt of glutamic acid N,N-diacetic acid in the chelating composition is at least about 47 weight percent based on a total weight of the chelating composition as determined using an Fe-Total Sequestering Value.

3. The method of claim 1 wherein the tetrasodium salt of glutamic acid N,N-diacetic acid present in the chelating composition in an amount of from about 47 to about 60 weight percent based on a total weight of the chelating composition as determined using an Fe-Total Sequestering Value.

4. The method of claim 1 further comprising the step of maintaining the temperature of the first combination at less than about 11° C.

5. The method of claim 1 wherein a temperature of the second combination is maintained at less than about 10° C.

and wherein the hydrogen cyanide is added to the first combination for a total time of about 15 to about 120 minutes.

6. The method of claim 1 wherein the step of combining monosodium glutamate and/or glutamic acid with formaldehyde is further defined as:

combining monosodium glutamate and/or glutamic acid with formaldehyde; and/or combining glutamic acid and caustic to form monosodium glutamate in situ and then combining the monosodium glutamate with formaldehyde; and/or combining glutamic acid and a disodium salt of glutamic acid to form monosodium glutamate in situ and then combining the monosodium glutamate with formaldehyde.

\*    \*    \*    \*    \*